US012605320B2

(12) United States Patent
Galle et al.

(10) Patent No.: US 12,605,320 B2
(45) Date of Patent: Apr. 21, 2026

(54) PHOTOPROTECTIVE COMPOSITION COMPRISING A GLYCINE BETAINE DERIVATIVE

(71) Applicant: SURFACTGREEN, Compiegne (FR)

(72) Inventors: Francis Galle, Rennes (FR); Freddy Pessel, Rennes (FR); Xavier Roussel, Le Mans (FR)

(73) Assignee: SURFACTGREEN, Compiegne (FR)

( * ) Notice: Subject to any disclaimer, the term of this patent is extended or adjusted under 35 U.S.C. 154(b) by 483 days.

(21) Appl. No.: 18/007,079

(22) PCT Filed: Jul. 29, 2021

(86) PCT No.: PCT/FR2021/051425
§ 371 (c)(1),
(2) Date: Jan. 27, 2023

(87) PCT Pub. No.: WO2022/023682
PCT Pub. Date: Feb. 3, 2022

(65) Prior Publication Data
US 2023/0310291 A1     Oct. 5, 2023

(30) Foreign Application Priority Data

Jul. 31, 2020     (FR) ...................................... 2008182

(51) Int. Cl.
*A61K 8/44*          (2006.01)
*A61Q 17/04*          (2006.01)

(52) U.S. Cl.
CPC ............... *A61K 8/44* (2013.01); *A61Q 17/04* (2013.01)

(58) Field of Classification Search
None
See application file for complete search history.

(56) References Cited

U.S. PATENT DOCUMENTS 6,224,852  B1 *   5/2001   Morgan ................. A61Q 17/04
                                                                      514/846
10,149,810  B2    12/2018   Perusse et al.

2010/0272662  A1 *  10/2010   Bonte ...................... A61Q 1/02
                                                                      424/64
2019/0380333  A1 *  12/2019   Pessel ...................... A61K 8/44
2022/0024855  A1 *   1/2022   Pessel ................... C07C 227/18

FOREIGN PATENT DOCUMENTS

FR          3 013 589          5/2015
WO      WO 2005/121294        12/2005
WO      WO-2020109710 A1 *     6/2020   ........... C07C 227/18

OTHER PUBLICATIONS

Goursaud, F. et al. "Glycine betaine as a renewable raw material to "greener" new cationic surfactants" *Green Chemistry*, Jan. 10, 2008, pp. 310-320, vol. 10, No. 3.
Kirilov, P. et al. "Cationic Surfactants Based on Renewable Raw Materials: New Emulsifiers for Elaboration of Nanoparticles of Dispersed Oil", poster, Mar. 23-26, 2010, pp. 1-2.
Anonymous "Instant Brightening Beauty Shot Eye Lift" Mintel Record ID 4026201, Jun. 2016, pp. 1-5.
Anonymous "Milk Bath Salts" Mintel Record ID 1150895, Aug. 2009, pp. 1-2.
Anonymous "Papaya Exfoliants Body Lotion" Mintel Record ID 1696661, Jan. 2012, pp. 1-3.
Nnanna, I. A. et al. "Potential Applications of Protein-Based Surfactants" *Protein-Based Surfactants*, Synthesis: Physicochemical Properties and Applications, Dekker, New York, NY, 2001, pp. 227-260, XP008174677.

* cited by examiner

*Primary Examiner* — Brian Gulledge
(74) *Attorney, Agent, or Firm* — SALIWANCHIK, LLOYD & EISENSCHENK

(57)          ABSTRACT

The present invention relates to a photoprotective composition comprising, in a physiologically acceptable medium, at least one photoprotective compound and a surfactant comprising at least one ester derivative or amide derivative of glycine betaine. It also relates to the cosmetic use of this photoprotective composition for protecting the skin against certain effects of UVA radiation, and also to this photoprotective composition for use thereof in the protection of the skin against erythema caused by UVB radiation. Finally, it relates to the use of the abovementioned surfactant for increasing the sand resistance of a photoprotective composition.

10 Claims, No Drawings

PHOTOPROTECTIVE COMPOSITION COMPRISING A GLYCINE BETAINE DERIVATIVE

CROSS-REFERENCE TO RELATED APPLICATION

This application is the U.S. national stage application of International Patent Application No. PCT/FR2021/051425, filed Jul. 29, 2021.

SUBJECT MATTER OF THE INVENTION

The present invention relates to a photoprotective composition comprising, in a physiologically acceptable medium, at least one photoprotective compound and a surfactant comprising at least one glycine betaine ester or amide derivative. It also relates to the cosmetic use of this photoprotective composition for protecting the skin against certain effects of UVA rays, and also to this photoprotective composition for its use in the protection of the skin against erythema due to UVB rays. Finally, it relates to the use of the abovementioned surfactant for increasing the resistance to sand of a photoprotective composition.

BACKGROUND OF THE INVENTION

In addition to being responsible for burns, UV rays are known to be involved in the production of free radicals which themselves lead to various detrimental changes of the skin, including skin aging phenomena, skin dryness, and also the formation of pigment spots and unevennesses of the complexion.

The photoprotective compositions used for protecting the skin against the effects of UV rays are generally provided in the form of an emulsion, of oil-in-water or water-in-oil type, which contains, at various concentrations, one or more lipophilic organic screening agents and/or inorganic nanopigments of metal oxides, capable of selectively absorbing harmful UV radiation, these screening agents and their amounts being selected according to the sun protection factor sought. In such emulsions, the hydrophilic screening agents are present in the aqueous phase and the lipophilic screening agents (often in the majority) are present in the fatty phase.

These emulsions generally include a large amount of oil necessary for the dissolution of the lipophilic UV screening agents and thus often exhibit a greasy and sticky feel liable to dissuade the consumer from their use. For this reason, oil-in-water emulsions are generally more appreciated by the consumer, in particular because of their pleasant feel and their presentation in non-fatty milk or cream form. However, they also more easily lose their effectiveness against UV rays as soon as they come into contact with water, when swimming in the sea or in a swimming pool, under the shower or when practicing water sports, insofar as hydrophilic screening agents tend to dissolve in water. Consequently, the antisun compositions which contain them, alone or combined with lipophilic screening agents, no longer provide the initial protection sought. Moreover, antisun compositions often exhibit poor resistance to sand, which affects their effectiveness at the seaside since the user is discouraged from renewing the applications on sandy skin. The grains of sand stuck to the skin also cause irritation during rubbing actions.

It would thus be useful to be able to have available photoprotective compositions exhibiting a nongreasy feel and good water resistance and/or resistance to sand.

It has already been proposed to use cationic surface-active agents to reduce the greasy feel of skin care compositions rich in oils and to improve the water resistance, but also the resistance to sand, of photoprotective compositions (HAPPI, December 2009, 62-65). However, a number of these compounds, in particular quaternary alkylammonium salts, such as distearyldimonium chloride and behentrimonium chloride, and also amidoquats, such as palmitamidopropyltrimonium chloride, exhibit inadequate biodegradability and inadequate ecotoxicity. There thus exists a need to develop photoprotective compositions which are more environmentally friendly.

Among biobased cationic agents, the use has already been suggested of an esterquat, distearoylethyldimonium chloride or DSEDC (Varisoft® from Evonik), in compositions for protection of the skin, in particular in antisun compositions. However, this compound can only be formulated in an acid medium and more specifically at a pH of less than 5 and generally of less than 4.5. However, the pH of healthy skin, which is determined by the constitution of the hydrolipidic film present at its surface, is on average 5.5. It would thus be desirable to have available compounds capable of being formulated in a wider pH range and in particular up to a pH of 5.5. Furthermore, the abovementioned cationic surfactants are not easily compatible with anionic additives, some of which are commonly used as dispersants for UV screening agents, which further increases their formulation constraints.

The applicant company has now discovered, unexpectedly and surprisingly, that certain glycine betaine derivatives make it possible to improve the resistance to sand of photoprotective compositions.

It has also been observed that these compounds can be formulated at a pH ranging up to 5.5 and in oil-rich compositions, without negatively affecting the stability or the sensory properties of these compositions.

These surfactants are furthermore biodegradable and exhibit a very low ecotoxicity, which is even lower than that of DSEDC.

The patent applications WO 2005/121294 and WO 2015/078893 describe leave-on cosmetic compositions, in particular antisun compositions, including glycine betaine ester or amide salts. In both cases, however, these glycine betaine derivatives are present in the form of surfactant compositions additionally including optionally cationized alkylpolyglycosides.

To the knowledge of the applicant company, however, it has never been suggested to use, for the abovementioned purposes, long-chain glycine betaine ester or amide salts, as is or in the form of surfactant compositions devoid of optionally cationized alkylpolyglycosides.

SUMMARY OF THE INVENTION

A subject matter of the invention is a photoprotective composition comprising, in a physiologically acceptable medium, at least one photoprotective compound and a surfactant comprising at least one glycine betaine derivative of formula (1): $[(CH_3)_3N^+—CH_2—COZ—R]_nX^{n-}$, where Z denotes an oxygen atom or an —NH group, R is a saturated or unsaturated, linear or branched, alkyl group comprising from 8 to 24 carbon atoms, X is an organic or inorganic anion and n has the value 1 or 2, it being understood that said photoprotective composition does not contain optionally cationized alkylpolyglycoside.

Another subject matter of the invention is the cosmetic use of the abovementioned photoprotective composition for protecting the skin against the effects of UVA rays chosen from: signs of skin aging, in particular wrinkles, sagging of the skin, loss of suppleness and/or of elasticity of the skin; roughness of the skin; loss of radiance of the complexion; nonuniformities of the complexion and in particular pigment spots; and/or drying of the skin.

A further subject matter of the invention is a cosmetic method for protecting the skin against the effects of UVA rays chosen from: signs of skin aging, in particular wrinkles, sagging of the skin, loss of suppleness and/or of elasticity of the skin; roughness of the skin; loss of radiance of the complexion; nonuniformities of the complexion and in particular pigment spots; and/or drying of the skin, comprising the topical application, to the skin, of the abovementioned photoprotective composition.

Another subject matter of this invention relates to a photoprotective composition as defined above, for its use in the protection of the skin against erythema due to UVB rays.

Yet another subject matter of the present invention relates to the use of a surfactant as defined above for increasing the resistance to sand of a photoprotective composition.

DETAILED DESCRIPTION

The present invention relates to a photoprotective composition including at least one glycine betaine derivative of given formula. The term "photoprotective composition" is understood to mean a composition including, in a physiologically acceptable medium, at least one photoprotective compound in an amount sufficient to block or absorb UV rays, preferably at least one organic or inorganic UVA and/or UVB screening agent. It generally confers, on the skin, protection against UV rays, determined by its Sun Protection Factor, of at least 15, indeed even of at least 30, for example a Sun Protection Factor of 15, 20, 30 or 50. It is a leave-on composition. The term "leave-on" is understood to mean that the composition is suitable for being and intended to be applied to the skin and left in place for at least one hour, before being removed by rinsing with water and/or using a cleaning composition.

This photoprotective composition includes a surfactant based on at least one glycine betaine derivative, which is a glycine betaine ester or amide salt. These two types of glycine betaine derivatives, and also their processes of preparation, will now be described in more detail.

Glycine Betaine Derivatives

I. Glycine Betaine Ester Salts

Glycine betaine ester salts can be obtained following a process comprising the successive stages consisting in:

(1) reacting glycine betaine or one of its salts with at least one saturated or unsaturated, linear or branched, fatty alcohol including from 8 to 24 carbon atoms, in the presence of an organic or inorganic acid;

(2) cooling the reaction medium to a temperature of 20 to 90° C.; and (3) recovering the surfactant composition thus obtained.

The first stage of this process consists in esterifying glycine betaine, or trimethylglycine. The glycine betaine can be of vegetable or synthetic origin. It is necessary to protonate it beforehand using an organic or inorganic acid, insofar as it exists in the zwitterionic form (presence of a carboxylate function). The acid can in particular be chosen from inorganic acids, such as hydrochloric acid, sulfuric acid, perhydric acids, such as perchloric acid, and their mixtures. In an alternative form, it can be chosen from organic acids, such as alkyl sulfuric acids, for example decyl or lauryl sulfuric acid; arylsulfonic acids, such as benzenesulfonic acid or para-toluenesulfonic acid; alkylsulfonic acids, such as triflic acid, methanesulfonic acid, ethanesulfonic acid, decylsulfonic acid, laurylsulfonic acid or camphorsulfonic acid; sulfosuccinic acid; and their mixtures. Lewis acids can also be used. Preferably, it is an alkylsulfonic acid and in particular methanesulfonic acid, insofar as it is easily biodegradable.

During the esterification, the acid function of the salified betaine is reacted with a fatty alcohol, to result in a glycine betaine ester in salt form. The term "fatty alcohol" is understood to mean a saturated or unsaturated, linear or branched (preferably linear), alcohol comprising from 8 to 24 carbon atoms. Examples of such fatty alcohols can be chosen from the group consisting of: octanol (C8:0), decanol (C10:0), undecanol (C11:0), lauryl alcohol (C12:0), myristyl alcohol (C14:0), cetyl alcohol (C16:0), palmitoleyl alcohol (C16:1), stearyl alcohol (C18:0), oleyl alcohol (C18:1), linoleyl alcohol (C18:2), linolenyl alcohol (C18:3), arachidyl alcohol (C20:0), arachidonyl alcohol (C20:4), behenyl alcohol (C22:0), 2-hexyldecanol, 2-octyldodecanol, 2-decyltetradecanol and their mixtures. Mixtures of fatty alcohols which can be used can be produced from one or more vegetable oils and in particular from soybean, olive, sunflower, corn, palm, copra, cottonseed, linseed, wheat, safflower or rapeseed oil, for example.

It is preferred according to the invention to use one or more alcohols including from 16 to 22 carbon atoms and more preferentially a mixture of such fatty alcohols.

The esterification reaction is generally carried out in the absence of solvent. The water produced during the reaction furthermore contributes to the dissolution of the glycine betaine in the reaction mixture.

For the implementation of this reaction, it is possible, for example, to use from 0.8 to 6.0 equivalents, preferably from 0.8 to 2 equivalents, for example from 0.9 to 1.0 equivalent, or in an alternative form from 1.1 to 1.8 equivalents, preferentially in this case from 1.2 to 1.6 equivalents and better still from 1.3 to 1.5 equivalents of fatty alcohol or, in a second alternative form, from 4.0 to 6.0 equivalents, preferentially in this case from 4.5 to 5.5 equivalents and better still from 4.8 to 5.2 equivalents of fatty alcohol.

In addition, use is advantageously made of 1.01 to 3.0 molar equivalents, preferably of 1.5 to 2.0 molar equivalents, for example of 1.5 to 1.9 molar equivalents, and preferentially of 1.5 to 1.7 molar equivalents of organic or inorganic acid, or in an alternative form of 1.02 to 1.08 molar equivalents, preferentially in this case of 1.03 to 1.07 molar equivalents and better still of 1.04 to 1.06 molar equivalents of organic or inorganic acid per 1 equivalent of glycine betaine. The esterification is carried out at a temperature ranging, for example, from 120 to 180° C., preferably from 150 to 180° C. The reaction can be carried out under atmospheric pressure or preferably under reduced pressure, for example at a pressure of 10 to 600 mbar. The pressure will generally become lower as the chain length of the fatty alcohol involved increases. The reaction medium is subsequently cooled to a temperature of 20 to 90° C.

The surfactant composition thus obtained is then recovered, which composition includes at least one glycine betaine ester salt of formula $[(CH_3)_3N^+—CH_2—COOR]_n$ $X^{n-}$, where: X is an organic or inorganic anion, R is an alkyl radical corresponding to the fatty alcohol R—OH employed in the esterification reaction, and n has the value 1 or 2.

The anion X results from the acid employed in the first stage of the process and can thus in particular be a chloride, a sulfate, a perchlorate, an alkyl sulfate ion, in particular a decyl sulfate or lauryl sulfate ion, an arylsulfonate ion, in particular a benzenesulfonate or para-toluenesulfonate ion, an alkylsulfonate ion, in particular a triflate, methanesulfonate, ethanesulfonate, decylsulfonate, laurylsulfonate or camphorsulfonate ion, or a sulfosuccinate ion. It is preferred according to the invention for X to be chosen from the alkylsulfonates and the arylsulfonates, in particular from the methanesulfonate, ethanesulfonate, triflate, para-toluenesulfonate and camphorsulfonate ions. It is advantageously the methanesulfonate ion.

The radical R can for its part be chosen from the octyl (C8:0), decyl (C10:0), undecyl (C11:0), lauryl (C12:0), myristyl (C14:0), cetyl (C16:0), palmitoleyl (C16:1), stearyl (C18:0), oleyl (C18:1), linoleyl (C18:2), linolenyl (C18:3), arachidyl (C20:0), arachidonyl (C20:4), behenyl (C22:0), 2-hexyldecyl, 2-octyldodecyl and 2-decyltetradecyl groups.

It is clearly understood that, in the case where several fatty alcohols are employed in the esterification reaction, the surfactant composition obtained will comprise several glycine betaine ester salts. The term "a glycine betaine ester salt" should thus be understood, in the context of this description and unless otherwise indicated, as referring to one or more of these salts.

The process described above makes it possible more specifically to obtain a surfactant composition including the following constituents:
(a) at least one glycine betaine ester salt of formula (1): [(CH$_3$)$_3$N$^+$—CH$_2$—COO—R]$_n$X$^{n-}$,
(b) at least one fatty alcohol of formula R—OH,
(c) an organic or inorganic acid of formula HX,
(d) a glycine betaine salt of formula [(CH$_3$)$_3$N$^+$—CH$_2$—COOH]$_n$X$^{n-}$, and
(e) optionally, at least one dialkyl ether of formula R—O—R,
where R is a saturated or unsaturated, linear or branched, alkyl group comprising from 8 to 24 carbon atoms and preferably from 16 to 22 carbon atoms, X is an organic or inorganic anion and n has the value 1 or 2.
This surfactant composition can be used as is in the present invention. In this case, it generally includes from 15% to 85% by weight of glycine betaine ester salt.

It is understood that, in the context of this description, the term "surfactant" is understood to mean both a glycine betaine ester salt as described here and the surfactant composition containing it, obtained as described above.

In a first alternative form, the surfactant composition includes:
(a) from 65% to 85% by weight, preferably from 70% to 80% by weight, of glycine betaine ester salt,
(b) from 1% to 20% by weight, for example from 1% to 9% by weight or from 10% to 20% by weight, of fatty alcohol,
(c) from 1% to 20% by weight, for example from 5% to 15% by weight, of organic or inorganic acid,
(d) from 1% to 20% by weight, for example from 2% to 15% by weight, of glycine betaine salt,
(e) from 0% to 15% by weight, for example from 2% to 10% by weight, of dialkyl ether.
In a second alternative form, the surfactant composition includes:
(a) from 15% to 45% by weight, preferably from 20% to 35% by weight, more preferably from 25% to 30% by weight, of glycine betaine ester salt, (b) from 50% to 70% by weight, for example from 60% to 70% by weight, of fatty alcohol,
(c) from 0% to 5% by weight, for example from 0% to 1% by weight, of organic or inorganic acid,
(d) from 0% to 3% by weight, for example from 0% to 1% by weight, of glycine betaine salt,
(e) from 0% to 15% by weight, for example from 2% to 10% by weight, of dialkyl ether.
Advantageously, the surfactant composition does not include a constituent other than the components (a) to (e) above. In an alternative form, the above process can include an additional stage consisting in isolating the glycine betaine ester salt present in this composition, which can be used as is in the present invention. In the latter case, the surfactant composition used according to the invention will comprise at least 90%, preferably at least 95%, indeed even at least 99%, by weight of glycine betaine derivative.

II. Glycine Betaine Amide Salts

These glycine betaine derivatives can be prepared following a process comprising the successive stages consisting in:
(1) reacting the glycine betaine or one of its salts with a saturated or unsaturated, linear or branched, C$_4$-C$_8$ alcohol in the presence of an organic or inorganic acid, at a temperature ranging, for example, from 100 to 180° C. and under reduced pressure;
(2) cooling the reaction medium to a temperature of 20 to 80° C.;
(3) adding one or more alkylamines including from 8 to 24 carbon atoms;
(4) removing the residual alcohol; and
(5) recovering the surfactant composition thus obtained.
The first stage of this process consists of an esterification reaction of the glycine betaine, which can be carried out in a similar way to the production of the glycine betaine esters, except that use is made of one or more linear and/or branched C$_4$-C$_8$ alcohol(s) in the presence of the acid, which can be chosen from those described above. Examples of such alcohols comprise butanol, pentanol, 3-methylbutan-1-ol (or isoamyl alcohol), fusel alcohol (mixture of pentanol, 2-methylbutan-1-ol and 3-methylbutan-1-ol), hexanol, heptanol, octanol and their mixtures. The term "butanol" is understood to mean equally well in this description n-butanol, isobutanol and sec-butanol. Butanol, and more particularly n-butanol, is preferred for use in this invention. This reaction is generally carried out in the absence of any solvent, the alcohol used constituting both the reactant and the medium. The water produced during the reaction also contributes to the dissolution of the glycine betaine in the reaction mixture. Use may generally be made of from 1.1 to 20 equivalents, for example from 2 to 4 equivalents, of linear or branched C$_4$-C$_8$ alcohol and of from 1.0 to 1.5 equivalents of sulfonic acid, for example from 1.0 to 1.2 equivalents and preferentially 1.1 equivalents of sulfonic acid, per 1 equivalent of glycine betaine. The esterification can be carried out at a temperature of 100 to 180° C., preferentially of 100 to 160° C., more preferentially of 120 to 150° C. or of 130 to 160° C., at atmospheric pressure or under reduced pressure.

The product of the esterification reaction may or may not be treated so as to separate the salt of the glycine betaine ester formed from the reaction medium. To do this, it is possible, for example, to carry out a filtration of the reaction medium, which makes it possible to separate the abovementioned salified ester, which is soluble in the alcohol, from the other constituents, which are not soluble.

One or more C$_8$-C$_{24}$ alkylamine(s) is/are subsequently added, either to the reaction medium or to the isolated ester. Examples of such amines are: octylamine, decylamine, laurylamine, tetradecylamine, hexadecylamine, octadecylamine, docosanylamine, eicosanylamine and their mixtures. It is preferred according to the invention to use one or more amines including from 16 to 22 carbon atoms and more preferentially a mixture of such amines.

In this stage, the alkylamine is advantageously used in the molten form. The amount of alkylamine(s) added can, for example, represent from 0.9 to 1.5 equivalents and preferably from 1.0 to 1.2 equivalents, per 1 equivalent of glycine betaine initially employed. This aminolysis reaction is typically carried out at a temperature of 50 to 180° C. and preferably of 120 to 140° C., under reduced pressure, for example under a pressure of 1 to 30 mbar. In parallel with the aminolysis reaction, the alcohol is removed by distillation under reduced pressure. The aminolysis reaction and the distillation take place over a period of time of 1 to 7 hours, in particular of 3 to 5 hours.

The surfactant composition thus obtained is then recovered.

This process makes it possible to obtain a surfactant composition comprising:

(a) one or more glycine betaine amide salt(s) of formula (1): $[(CH_3)_3N^+—CH_2—CONH—R]_nX^{n-}$;

(b) one or more alkylammonium salt(s) of formula (2): $[NH_3^+R]_nX^{n-}$;

(c) one or more glycine betaine ester salt(s) of formula (3): $[(CH_3)_3N^+—CH_2—COOR']_nX^{n-}$, where R' is a saturated or unsaturated, linear or branched, alkyl radical containing from 4 to 8 carbon atoms; and (d) glycine betaine of formula (4): $(CH_3)_3N^+—CH_2—COO^-$;

where R is a saturated or unsaturated, linear or branched, alkyl group comprising from 8 to 24 carbon atoms, preferably from 16 to 22 carbon atoms, X is an organic or inorganic anion and n has the value 1 or 2.

It is understood that, in the context of this description, the term "surfactant" is understood to mean both a glycine betaine amide salt as described here and the surfactant composition containing it, obtained as described above.

This surfactant composition can be used as is in the present invention. In this case, it generally includes from 60% to 98% by weight, for example from 70% to 80% by weight, of glycine betaine amide salt. The constituent (b) can represent from 0% to 25% by weight, for example from 15% to 20% by weight, the constituent (c) from 0% to 15% by weight, for example from 5% to 10% by weight, and the constituent (d) from 0% to 5% by weight, with respect to the total weight of the surfactant composition. Advantageously, the latter does not include a constituent other than the components (a) to (d) above. In an alternative form, the above process can include an additional stage consisting in isolating the glycine betaine amide salt present in this composition, which can be used as is in the present invention. In the latter case, the surfactant composition will comprise at least 90%, preferably at least 95%, indeed even at least 99%, by weight of glycine betaine derivative.

It is preferred in all cases for the surfactant composition including a glycine betaine ester or amide salt as defined above, and/or the photoprotective composition comprising it, not to contain an optionally cationized alkylpolyglycoside.

For use in the present invention, glycine betaine ester salts and in particular the salts of esters including from 14 to 22 carbon atoms, preferably from 16 to 22 carbon atoms and more preferentially from 18 to 22 carbon atoms are preferred.

Photoprotective Compositions

For the implementation of the present invention, use is made of a photoprotective composition including a surfactant as described above, preferably in an amount of 1% to 15% by weight, more preferably of 2% to 8% by weight, with respect to the weight of the photoprotective composition, when it is a surfactant composition as described above. The photoprotective composition generally includes from 0.5% to 8% by weight and preferentially from 1% to 5% by weight of glycine betaine derivative according to the invention.

The photoprotective composition includes a physiologically acceptable medium, that is to say a medium compatible with the skin, in particular a cosmetically acceptable medium, that is to say a medium which does not generate tingling or redness incompatible with a cosmetic use. This medium preferably includes an aqueous phase, including water and/or glycerol, and a fatty phase to form an emulsion. This emulsion can be of the oil-in-water (O/W), oil-in-glycerol, water-in-oil (W/O), water-in-glycerol or multiple (for example W/0/W) type. This emulsion is preferentially of the oil-in-water type.

The aqueous phase can additionally include at least one aqueous gelling agent. The term "aqueous gelling agent" denotes a polymeric compound capable of immobilizing water molecules by becoming hydrated and of thus increasing the viscosity of the aqueous phase. Such a gelling agent can be chosen from: polysaccharides, such as cellulose and its derivatives, modified starches, carrageenan, agar agar, xanthan gum and vegetable gums, such as guar, tara or locust bean gum; synthetic polymers and in particular optionally crosslinked sodium acrylate homopolymers, and also acrylic copolymers, in particular copolymers of sodium acrylate and/or of alkyl (meth)acrylate and/or of hydroxyalkyl (meth)acrylate and/or of (polyethoxy)alkyl (meth) acrylate, with optionally at least one other monomer, advantageously 2-acrylamido-2-methylpropanesulfonic acid (AMPS), these copolymers optionally being crosslinked; and their mixtures.

For its part, the fatty phase can comprise one or more volatile and/or nonvolatile oils. Examples of volatile oils are branched alkanes, such as isododecane, and linear $C_{10}$-$C_{13}$ alkanes. Mention may in particular be made, as nonvolatile oils, of:

esters of acids and of monoalcohol chosen from: mono- and polyesters of saturated linear $C_2$-$C_{10}$ (preferably $C_6$-$C_{10}$) acids and of saturated linear $C_{10}$-$C_{18}$ (preferably $C_{10}$-$C_{14}$) monoalcohols, mono- and polyesters of saturated linear $C_{10}$-$C_{20}$ acids and of branched or unsaturated $C_3$-$C_{20}$ (preferably $C_3$-$C_{10}$) monoalcohols; mono- and polyesters of branched or unsaturated $C_5$-$C_{20}$ acids and of branched or unsaturated $C_5$-$C_{20}$ monoalcohols; mono- and polyesters of branched or unsaturated $C_5$-$C_{20}$ acids and of linear $C_2$-$C_4$ monoalcohols;

triglycerides of $C_6$-$C_{12}$ fatty acids, such as triglycerides of caprylic and capric acids, and triheptanoin;

branched and/or unsaturated $C_{10}$-$C_{20}$ fatty acids (such as linoleic acid);

branched and/or unsaturated $C_{10}$-$C_{20}$ fatty alcohols (such as octyldodecanol and oleyl alcohol);

hydrocarbons, such as squalane ($C_{30}$), in particular vegetable squalane extracted from olive oil, and hemisqualane ($C_{15}$);

dialkyl carbonates, such as dicaprylyl carbonate and diethylhexyl carbonate;

dialkyl ethers, such as dicaprylyl ether; and their mixtures.

Mention may also be made of vegetable oils which contain one or more of the abovementioned constituents.

Mention may in particular be made, as esters of acids and of monoalcohols, of monoesters, such as the coco-caprate/caprylate mixture, ethyl macadamiate, the ethyl ester of shea butter, isostearyl isostearate, isononyl isononanoate, ethylhexyl isononanoate, hexyl neopentanoate, ethylhexyl neopentanoate, isostearyl neopentanoate, isodecyl neopentanoate, isopropyl myristate, octyldodecyl myristate, isopropyl palmitate, ethylhexyl palmitate, hexyl laurate, isoamyl laurate, cetostearyl nonanoate, propylheptyl caprylate and their mixtures. Other esters which can be used are diesters of acids and of monoalcohols, such as diisopropyl adipate, diethylhexyl adipate, diisopropyl sebacate and diisoamyl sebacate.

Examples of vegetable oils are in particular wheat germ, sunflower, linseed, argan, hibiscus, coriander, grape seed, corn, apricot, castor, shea, avocado, olive, soybean, sweet almond, palm, rapeseed, cottonseed, hazelnut, macadamia, jojoba, alfalfa, poppy, red kuri squash, sesame, pumpkin, blackcurrant, evening primrose, lavender, borage, millet, barley, quinoa, rye, safflower, candlenut, passionflower, muscat rose, echium, camelina or camellia oil.

The fatty phase can additionally comprise at least one fatty phase structuring agent. The term "fatty phase structuring agent" is understood to mean a compound capable of thickening the oils contained in the composition, chosen in particular from waxes, fatty phase gelling agents and pasty fatty substances, and also their mixtures.

In one embodiment of the invention, the photoprotective composition includes at least 20% by weight, preferably at least 30% by weight, more preferentially at least 40% by weight, indeed even at least 50% by weight, of oil(s). In some embodiments, the photoprotective composition can even comprise at least 60%, for example at least 70%, indeed even at least 80%, by weight of oil(s). This is because it has been observed that the glycine betaine derivatives according to the invention make it possible to confer a nongreasy, indeed even powdery, feel on these compositions, even though they include a high content of oil(s).

The photoprotective composition includes at least one organic or inorganic UV screening agent, or a mixture of them, preferably at least one insoluble UV screening agent. The term "UV screening agent" is understood to mean any system capable of screening out UVA and/or UVB radiation. The term "insoluble UV screening agent" is understood to mean, within the meaning of the present invention, UV screening agents which are insoluble in the cosmetic media generally used in antisun formulations and more particularly the solubility of which in water at 25° C. is less than 0.1% by weight and the solubility of which in liquid paraffin at 25° C. is less than 1% by weight.

UV screening agents can be UVB screening agents (absorption in the range from 290 to 320 nm), UVA screening agents (absorption in the range from 320 to 380 nm) or broad-spectrum screening agents (absorption in the range from 290 to 380 nm). Generally, it is preferred to use a combination of at least two UV screening agents, preferentially of at least one UVA screening agent and of at least one UVB screening agent.

Mention may be made, as examples of organic UV screening agents, of those which follow, designated by their INCI names:

Butyl Methoxydibenzoylmethane or Avobenzone para-Aminobenzoic acid (PABA) and its derivatives, such as Ethyl PABA, Ethyl dihydroxypropyl PABA, Ethylhexyl dimethyl PABA, Glyceryl PABA, PEG-25 PABA Salicylic acid derivatives, including: Homosalate, Ethylhexyl salicylate, Dipropylene glycol salicylate, TEA salicylate β,β-Diphenylacrylate derivatives, such as Octocrylene, Etocrylene Benzophenone derivatives, including Benzophenone-1, Benzophenone-2, Benzophenone-3, Benzophenone-4, Benzophenone-5, Benzophenone-6, Benzophenone-8, Benzophenone-9, Benzophenone-12

Diethylaminohydroxybenzoylhexyl benzoate ("Uvinul A Plus" from BASF)

Benzylidenecamphor derivatives, such as 3-Benzylidenecamphor, 4-Methylbenzylidenecamphor ("Eusolex 6300" from Merck), Benzylidenecamphorsulfonic acid, Camphor benzalkonium methosulfate, Terephthalylidenedicamphorsulfonic acid, Polyacrylamidomethylbenzylidenecamphor Phenylbenzimidazole derivatives, including Phenylbenzimidazolesulfonic acid ("Eusolex 232" from Merck), Disodium phenyl dibenzimidazole tetrasulfonate Phenylbenzotriazole derivatives, including Drometrizole trisiloxane, Methylenebis(benzotriazolyl)tetramethylbutylphenol ("Tinosorb M" from Ciba)

Triazine derivatives, such as Bis(ethylhexyloxyphenol) methoxyphenyl triazine ("Tinosorb S" from Ciba), Ethylhexyltriazone ("Uvinul T150" from BASF), Diethylhexylbutamidotriazone ("Uvasorb HEB" from Sigma 3V), 2,4,6-tris(diisobutyl 4'-aminobenzalmalonate)-s-triazine Anthranilic derivatives, including Menthyl anthranilate Imidazoline derivatives, such as Ethylhexyldimethoxybenzylidenedioxoimidazoline propionate Benzylmalonate derivatives, such as polyorganosiloxanes containing benzylmalonate functions, in particular Polysilicone-15 ("Parsol SLX" from Hoffmann-LaRoche)

4,4-Diarylbutadiene derivatives, including 1,1-Dicarboxy (2,2'-dimethylpropyl)-4,4-diphenyl-butadiene Benzoxazole derivatives, such as 2,4-bis[5-(1-dimethylpropyl)benzoxazol-2-yl(4-phenyl)imino]-6-(2-ethylhexyl)imino-1,3,5-triazine ("Uvasorb K2A" from Sigma 3V)

Merocyanine derivatives, such as those described in WO 2004006878 and their mixtures.

The UV screening agents are generally used in the photoprotective composition according to the invention in an amount of 0.05% to 30% by weight, preferably of 5% to 25% by weight, more preferentially of 10% to 20% by weight, with respect to the total weight of the photoprotective composition.

According to a preferred embodiment, this photoprotective composition additionally includes at least one antiaging active principle, in particular an active principle suitable for preventing and/or treating wrinkles, sagging of the skin and/or the formation of pigment spots, which can in particular be chosen from agents for combating free radicals or antioxidants, agents which stimulate the differentiation and/or the proliferation of keratinocytes and/or fibroblasts; agents which stimulate the synthesis of glycosaminoglycans and/or collagen and/or dermoepidermal anchoring fibrils and/or elastic fibers; agents which prevent the degradation of collagen and/or glycosaminoglycans and/or dermoepidermal anchoring fibrils and/or elastic fibers; antiglycation agents; depigmenting and/or melanogenesis-inhibiting agents; and their mixtures.

Examples of such antiaging active principles are in particular: ascorbic acid, its salts, its ethers and its esters, in particular ascorbyl glucoside; adenosine; vegetable proteins and their hydrolysates; polypeptides and pseudodipeptides; silanes, such as methylsilanol mannuronate; α- and β-hydroxy acids; and their mixtures.

According to an advantageous embodiment of the invention, the photoprotective composition comprises at least one antioxidizing active principle, which makes it possible to limit the oxidative damage caused by UV rays, in particular vitamins, such as ascorbic acid and its derivatives and tocopherol and its derivatives, ubiquinone or coenzyme Q10, polyphenols, such as resveratrol and its derivatives, and also plant extracts containing them, in particular pomegranate, grape or green tea extracts; carotenoids, such as lycopene, and also plant extracts containing them; and their mixtures.

The photoprotective composition according to the invention can also include at least one self-tanning agent, such as DHA and/or erythrulose.

As an alternative form or in addition, the photoprotective composition according to the invention can comprise at least one moisturizing or humectant agent, chosen for example from polyols, such as propylene glycol, glycerol, pentylene glycol, xylitol or sorbitol; urea; hyaluronic acid and its salts; amino acids; and their mixtures.

The photoprotective composition according to the invention can additionally contain various constituents which can be dispersed in the fatty phase and/or in the aqueous phase which it includes, provided that these are compatible with topical application to the skin.

It can thus include at least one oil-in-water or water-in-oil emulsifier which is generally nonionic, such as polyoxyethylene esters, optionally polyethoxylated sorbitan esters, optionally polyethoxylated esters of fatty acids and of glycerol, sucrose esters, ethers of fatty alcohols and of sugar, such as alkyl glucosides, and their mixtures. The emulsifiers can represent from 2% to 10% and preferably from 4% to 6% of the total weight of the composition.

In one embodiment of the invention, the photoprotective composition does not include an emulsifier other than the surfactant composition described above. In particular, in the case of glycine betaine esters, the surfactant composition containing them in addition naturally includes a more or less large amount of fatty alcohol which confers noteworthy emulsifying properties on it.

The photoprotective composition according to the invention can additionally comprise additives chosen in particular from: pulverulent fillers; fragrances; sequestering agents; pH adjusters; preservatives; pigments; dyes; and their mixtures.

Examples of pH adjusters are acetic acid/sodium acetate and succinic acid/sodium succinate buffer solutions, sodium gluconate and sodium lactate. The pH of the photoprotective composition can in particular be between 2 and 6, preferably between 4 and 5.5 and better still between 5 and 5.5.

The photoprotective composition can have a liquid or semiliquid consistency or a solid consistency. It can be provided in any form suitable for topical application to the skin and in particular in the milk, cream, lotion or gel form.

It can in particular be packaged in a tube, a pump-action spray or a jar. In an alternative form, it can be packaged in an aerosol container, in order to ensure application of the composition in vaporized form. In the latter case, the photoprotective composition preferably comprises at least one propellant.

12

Use

The photoprotective composition according to the invention is suitable for being and intended to be applied to the skin. The term "skin" is understood to mean all of the skin of the body with the exclusion of the scalp and in particular the face, neck, neckline, hands, arms, legs and/or stomach.

It can be applied to the skin one or more times per day, for the purpose of protecting it against the effects of UV rays, in particular against erythema due to UVB rays, and/or to prevent and/or slow down the detrimental change in the appearance of the skin caused by its exposure to UVA rays, in particular to prevent and/or slow down signs of skin aging, in particular wrinkles, sagging of the skin, loss of suppleness and/or of elasticity of the skin; roughness of the skin; loss of radiance of the complexion; nonuniformities of the complexion and in particular pigment spots; and/or drying of the skin.

The surfactant according to the invention makes it possible to increase the resistance to sand of the photoprotective composition.

The capacity of resistance to sand of the photoprotective compositions according to the invention can be evaluated by applying 0.3 g of composition to the forearm of a panelist and then, after one minute, by spraying fine sand (30 ml) over the treated surface. In an alternative form, the modified application protocol described in the examples below can be used. The panelist subsequently claps his/her hands three times to remove the sand. The sand remaining on the forearm is then recovered by rinsing, dried and weighed.

The surfactant according to the invention can also increase the water resistance of the photoprotective composition. This is because the cationic charge of this surfactant exhibits a certain affinity for the keratin of the skin (overall negatively charged), thus making it possible to form a hydrophobic film on the skin (by virtue of the lipophilic chains of the surfactant) which creates a barrier to water.

The water resistance of the photoprotective compositions according to the invention can be measured according to two methods. In the first method, the water resistance is evaluated in vitro by measuring the contact angle of a drop of water on a surface coated with the photoprotective composition. The second method consists in carrying out the in vivo test recommended by COLIPA in "Guidelines for Evaluating Sun Product Water Resistance (December 2005)", that is to say in measuring the ratio of the SPF after action of the water compared to the SPF before action of the water. The SPF reflects the increase in the duration of solar irradiation made possible by using the composition. It corresponds to the quotient of the duration to reach the erythemal threshold (minimal erythemal dose or MED) in the presence of the photoprotective composition (protected skin) with respect to the duration measured in the absence of this composition (unprotected skin). The SPF is determined in vivo on human skin in accordance with the instructions of COLIPA. The MED is the lowest dose of UV irradiation which, after 16-24 h, generates a slight but clear redness of the skin (sunburn, erythema). The irradiation sources are generally xenon lamps.

Whatever the surfactant used (based on glycine betaine ester or amide), the surfactant composition used according to the invention can additionally protect the skin against the cutaneous effects of external attacks. The term "external attacks" is understood to mean in particular compositions for cleaning the skin, more particularly those containing at least one anionic surfactant, and/or environmental factors, such as atmospheric pollutants and/or electromagnetic radiation with a wavelength of between 280 and 500 nm, namely UV rays and blue light.

Pollutants, but also UV rays and blue light, are in particular liable to lead to excessive production of free radials responsible for skin aging phenomena. The main atmospheric pollutants which can have a deleterious effect on the skin are toxic gases (such as ozone, carbon monoxide, nitrogen oxides or sulfur oxides), heavy metals, present in particular in cigarette smoke (such as mercury, cadmium or lead), polycyclic aromatic hydrocarbons (or "PAHs", such as benzopyrene) and fine particles, such as PM2.5, which are combustion residues on which a large amount of organic and inorganic compounds are adsorbed. For their part, anionic surfactants, and in particular the sulfates used in hygiene and cleaning products, themselves also tend to dry out the skin. Finally, the various chemical and physical attacks to which the skin is subjected continuously modify the speed and quality of renewal of the epidermis. A detrimental change in the barrier function is thus observed, which is expressed by various visible signs, such as dry skin, the formation of superficial or deeper furrows, a dull complexion and/or the appearance of pigment spots.

The surfactant described above can thus make it possible to prevent and/or slow down the detrimental change in the appearance of the skin caused by external attacks. It can thus also be used in leave-on cosmetic compositions, in particular cosmetic compositions for caring for the skin or for make up (such as a foundation).

A better understanding of the invention will be obtained in the light of the following examples, which are given purely by way of illustration without the aim of limiting the scope of the invention, defined by the appended claims.

EXAMPLES

Example 1: Test of Resistance to Sand

The effect of a surfactant composition according to the invention on the resistance to sand of a photoprotective composition was evaluated.

1—Preparation of the Surfactant Composition

Glycine betaine (1.0 eq) and a mixture of $C_{18}$ to $C_{22}$ fatty alcohols (5.0 eq) are introduced into a reactor. The setpoint temperature in the mixture is fixed at 150° C. and the pressure is reduced down to a value of 60 mbar. Once the pressure and temperature setpoints have been reached, a 70% methanesulfonic acid solution (1.05 eq) is added to the reaction mixture. As soon as the addition is complete, the setpoint temperature is brought back to 150° C. and the pressure is maintained at a value of 30 mbar. Six hours after the start of the introduction of the acid, the reaction mixture is allowed to cool to 80° C., then the product is recovered, cooled down to ambient temperature, and the constitutes the surfactant composition according to the invention, which includes the following constituents:

| | Composition by weight |
| --- | --- |
| $C_{18}$-$C_{22}$ Alkyl betainate mesylate | 25.8% |
| Glycine betaine mesylate | 0.3% |
| $C_{18}$-$C_{22}$ Fatty alcohols | 65.1% |

-continued

| | Composition by weight |
| --- | --- |
| Methanesulfonic acid | 0.7% |
| $C_{18}$-$C_{22}$ Alkyl ethers | 8.2% |

2—Preparation of the Photoprotective Compositions

Two photoprotective compositions were prepared in the form of O/W emulsions containing the following constituents:

| | Amount (% by weight) | |
| --- | --- | --- |
| Constituent (INCI name) | Composition A | Composition B |
| Hydroxyethylcellulose | 0.5% | 0.5% |
| Glycerin | 3.0% | 3.0% |
| Stearyl/Behenyl Betainate Mesylate (and) Stearyl/Behenyl Alcohol[1] | 6.0% | |
| Behentrimonium Chloride | | 1.98% |
| Arachidyl (and) Behenyl Alcohol | | 4.02% |
| Methylene Bis-Benzotriazolyl Tetramethylbutylphenol (and) Aqua (and) Decyl Glucoside (and) Propylene Glycol (and) Xanthan Gum[2] | 4.0% | 4.0% |
| Butyl Methoxydibenzoylmethane | 3.0% | 3.0% |
| Bis-Ethylhexyloxyphenol Methoxyphenyl Triazine | 6.0% | 6.0% |
| Ethylhexyl Salicylate | 3.0% | 3.0% |
| C12-15 Alkyl Benzoate | 6.0% | 6.0% |
| Caprylic/Capric Triglycerides | 6.0% | 6.0% |
| Butyrospermum Parkii Butter | 2.0% | 2.0% |
| Persea Gratissima (Avocado) Oil | 2.0% | 2.0% |
| Sodium Benzoate (and) Potassium Sorbate (and) Aqua | 0.8% | 0.8% |
| Aqua | q.s. for 100% | q.s. for 100% |

[1]Surfactant composition according to the invention, prepared as described above.
[2]Parsol Max ® from DSM

3—Test of Resistance to Sand

The resistance to sand of compositions A and B above was evaluated.

To do this, 10 g of sand were sprinkled over a flat surface. At the same time, a 7×4 cm rectangle was traced on the forearm of volunteers, in which 56 g of composition A or B were subsequently applied (in a proportion of 2 mg/cm$^2$). The cream was caused to penetrate by gentle massaging and then the arm was left in the open air for 2 min. The forearm was then applied to the sand for 10 sec. After a leave-on time of 1 min, the volunteers were asked to clap their hands three times with the same force. The amount of sand which remained stuck to the forearm was subsequently calculated.

Three tests were carried out. The mean of these tests was calculated and is reported in the table below:

| | Composition A | Composition B |
| --- | --- | --- |
| Mean | 54.87% | 64.47% |
| Standard deviation | 1.03% | 1.26% |

It emerges from these tests that the surfactant composition according to the invention confers, on the photoprotective composition, a resistance to sand which is significantly greater than that of other cationic surfactants.

Example 2: Antisun Compositions

Several types of antisun products can be prepared using surfactant compositions according to the invention, hereinafter identified by GBE or GBA, based respectively on glycine betaine ester or amide salts.

Antisun Cream:

| Starting Material | INCI | % Matter |
|---|---|---|
| Demineralized water | Aqua | q.s. for 100 |
| Natrosol 250 HHR | Hydroxyethylcellulose | 0.5 |
| Glycerol | Glycerin | 4 |
| Tegosoft TN | C12-15 Alkyl Benzoate | 5 |
| Cocoa butter | Theobroma Cacao Seed Butter | 1.5 |
| Emogreen L15 | C15-19 Alkane | 2 |
| Dermosoft GMCY | Glyceryl Caprylate | 0.5 |
| Liponate PC | Propylene Glycol Dicaprylate/Dicaprate | 2 |
| Candelilla Wax | Euphorbia Cerifera (Candelilla) Wax | 1 |
| Tegin M Pellets | Glyceryl Stearate | 1 |
| Lipovol C-76 | Cocos Nucifera (Coconut) Oil | 1 |
| Parsol 1789 | Butyl Methoxydibenzoylmethane | 2 |
| Parsol SHIELD | Bis-Ethylhexyloxyphenol Methoxyphenyl Triazine | 6 |
| Mfsorb 507 | Ethylhexyl Triazone | 2 |
| Parsol Max | Methylene Bis-Benzotriazolyl Tetramethylbutylphenol (and) Aqua (and) Decyl Glucoside (and) Propylene Glycol (and) Xanthan Gum | 5 |
| GBAC16C22 | — | 6 |
| Optiphen 300 | Phenoxyethanol (and) Caprylyl Glycol | 0.8 |
| Wheat starch | Triticum Vulgare Starch | 2 |
| 30% Sodium gluconate solution | Sodium Gluconate (and) Aqua | 13 |

Solid Antisun Cream SPF25:

| Starting Material | INCI | % Matter |
|---|---|---|
| Tegosoft TN | C12-15 Alkyl Benzoate | 6 |
| Parsol SHIELD | Bis-Ethylhexyloxyphenol Methoxyphenyl Triazine | 6 |
| Parsol 1789 | Butyl Methoxydibenzoylmethane | 3 |
| Parsol Max | Methylene Bis-Benzotriazolyl Tetramethylbutylphenol (and) Aqua (and) Decyl Glucoside (and) Propylene Glycol (and) Xanthan Gum | 4 |
| Parson EHS | Ethylhexyl Salicylate | 3 |
| 1-Octadecanol | Stearyl Alcohol | 20 |
| Myritol 318 | Caprylic/Capric Triglyceride | 10 |
| Kokum butter | Garnicia Indica Seed Butter | 15 |
| Avocat HV 1654 | Persea Gratissima (Avocado) Oil | 6 |
| Emogreen L19 | C15-19 Alkane | 8 |
| CosmeGreen ES1822+ | Arachidyl/Behenyl Betainate Mesylate (and) Arachidyl/Behenyl Alcohol | 15 |
| Lactate/lactic buffer solution pH = 4.27 | Sodium Lactate (and) Lactic Acid (and) Aqua | 4 |

Cosmos SPF30 Antisun Cream:

| Starting Material | INCI | % Matter |
|---|---|---|
| Cosmos Z75 | Zinc Oxide (and) Dicaprylyl Carbonate (and) Polyhydroxy Stearic Acid (and) Stearic Acid | 18 |
| SFT-85-CC | Titanium Dioxide (and) Silica (and) Jojoba Esters (and) Dicaprylyl Carbonate (and) Polyhydroxystearic Acid | 25 |
| CosmeGreen MB1618 | Cetearyl Betainate Mesylate (and) Cetearyl Alcohol | 15 |
| 1-Octadecanol | Stearyl Alcohol | 20 |
| Emogreen L15 | C15-19 Alkane | 4 |
| Shea butter B1646 | Butyrospermum Parkii Butter | 10 |
| Myritol 318 | Caprylic/Capric Triglyceride | 4 |
| Lactate/lactic buffer solution pH = 4.27 | Sodium Lactate (and) Lactic Acid (and) Aqua | 4 |

The invention claimed is:

1. A photoprotective composition which is a leave-on composition comprising, in a physiologically acceptable medium, at least one photoprotective compound and a surfactant comprising at least one glycine betaine derivative, it being understood that said photoprotective composition does not contain optionally cationized alkylpolyglycoside, wherein the surfactant includes the following constituents:

(a) at least one glycine betaine ester salt of formula (1):
$[(CH_3)_3N^+\!-\!CH_2\!-\!COO\!-\!R]_nX^{n-}$, (b) at least one fatty alcohol of formula R—OH, (c) an organic or inorganic acid of formula HX, and (d) a glycine betaine salt of formula $[(CH_3)_3N^+\!-\!CH_2\!-\!COOH]_nX^{n-}$, where R is a saturated or unsaturated, linear or branched, alkyl group comprising from 8 to 24 carbon atoms, X is an organic or inorganic anion and n has the value 1 or 2.

2. The photoprotective composition as claimed in claim 1, wherein the radical R is selected from the group consisting of octyl ($C_{8:0}$), decyl (C10:0), undecyl (C11:0), lauryl (C12:0), myristyl (C14:0), cetyl (C16:0), palmitoleyl (C16:1), stearyl (C18:0), oleyl (C18:1), linoleyl (C18:2), linolenyl (C18:3), arachidyl (C20:0), arachidonyl (C20:4), behenyl (C22:0), 2-hexyldecyl, 2-octyldodecyl and 2-decyltetradecyl groups.

3. The photoprotective composition as claimed in claim 1, wherein the anion X is selected from the group consisting of a chloride, a sulfate, a perchlorate, an alkyl sulfate ion, an arylsulfonate ion, an alkylsulfonate ion, and a sulfosuccinate ion.

4. The photoprotective composition as claimed in claim 3, wherein the anion X is selected from the group consisting of the methanesulfonate, ethanesulfonate, triflate, para-toluenesulfonate and camphorsulfonate ions.

5. The photoprotective composition as claimed in claim 1, wherein the surfactant consists of the claimed constituents.

6. The photoprotective composition as claimed in claim 1, wherein R comprises from 16 to 22 carbon atoms.

7. The photoprotective composition as claimed in claim 1, for protecting the skin against erythema due to UVB rays.

8. A cosmetic method for protecting the skin against the effects of UVA rays selected from: signs of skin aging, in particular wrinkles, sagging of the skin, loss of suppleness and/or of elasticity of the skin; roughness of the skin; loss of radiance of the complexion; nonuniformities of the complexion and in particular pigment spots; and/or drying of the skin, comprising the topical application, to the skin, of the photoprotective composition as claimed in claim 1.

9. The cosmetic method of claim 8, wherein the photoprotective composition is applied to the face, neck, neckline, hands, arms, legs and/or stomach.

10. A method for increasing the resistance to sand of a photoprotective composition comprising adding thereto at least one surfactant comprising at least one glycine betaine derivative, wherein the surfactant includes the following constituents:

(a) at least one glycine betaine ester salt of formula (1):
$[(CH_3)_3N^+\!-\!CH_2\!-\!COO\!-\!R]_nX^{n-}$, (b) at least one fatty alcohol of formula R—OH, (c) an organic or inorganic acid of formula HX, and (d) a glycine betaine salt of formula $[(CH_3)_3N^+\!-\!CH_2\!-\!COOH]_nX^{n-}$, where R is a saturated or unsaturated, linear or branched, alkyl group comprising from 8 to 24 carbon atoms, X is an organic or inorganic anion and n has the value 1 or 2.

* * * * *